United States Patent
Margulies et al.

(10) Patent No.: US 6,679,890 B2
(45) Date of Patent: Jan. 20, 2004

(54) METHOD AND APPARATUS FOR AUGMENTATION OF THE FEMORAL NECK

(76) Inventors: Joseph Y. Margulies, 8 Usonia Rd., Pleasantville, NY (US) 10570; Gamal Baroud, 3803 Ave. Laval, Montreal, Quebec (CA), H2W 2H9; Thomas Steffen, Breitfeldstrasse 4, Bern (CH), CH-3014; Max Aebi, Rathausplatz 4, Bern (CH), CH-3011

(*) Notice: Subject to any disclaimer, the term of this patent is extended or adjusted under 35 U.S.C. 154(b) by 0 days.

(21) Appl. No.: 10/199,090

(22) Filed: Jul. 22, 2002

(65) Prior Publication Data

US 2003/0045885 A1 Mar. 6, 2003

Related U.S. Application Data

(60) Provisional application No. 60/315,577, filed on Aug. 28, 2001.

(51) Int. Cl.[7] ............................. A61F 2/00; A61B 17/58
(52) U.S. Cl. ............................. 606/94; 606/60; 606/62; 606/92
(58) Field of Search ............................. 606/60, 62, 67, 606/72, 73, 92–94

(56) References Cited

U.S. PATENT DOCUMENTS

| | | | | |
|---|---|---|---|---|
| 4,274,163 A | | 6/1981 | Malcom et al. ............... 3/1.91 |
| 4,462,394 A | * | 7/1984 | Jacobs ............................. 606/94 |
| 4,494,535 A | | 1/1985 | Haig ............................. 128/92 BA |
| 4,653,487 A | | 3/1987 | Maale ............................. 128/92 VQ |
| 4,653,489 A | | 3/1987 | Tronzo ............................. 128/92 YV |
| 5,047,030 A | * | 9/1991 | Draenert ............................. 606/65 |
| 5,102,413 A | | 4/1992 | Poddar ............................. 606/62 |
| 5,514,137 A | * | 5/1996 | Coutts ............................. 606/92 |
| 5,562,704 A | | 10/1996 | Tamminmaki et al. ....... 606/213 |
| 5,759,184 A | | 6/1998 | Santangelo ............................. 606/68 |
| 5,772,662 A | * | 6/1998 | Chapman et al. .............. 606/69 |
| 5,810,821 A | * | 9/1998 | Vandewalle ............................. 606/65 |
| 5,824,087 A | | 10/1998 | Aspden et al. ............................. 623/16 |
| 5,976,139 A | * | 11/1999 | Bramlet ............................. 606/66 |
| 6,197,031 B1 | * | 3/2001 | Barrette et al. ............... 606/80 |
| 6,375,659 B1 | * | 4/2002 | Erbe et al. ............................. 606/94 |
| 6,488,684 B2 | * | 12/2002 | Bramlet et al. ............... 606/62 |

* cited by examiner

*Primary Examiner*—Gary Jackson
(74) *Attorney, Agent, or Firm*—Leonard Cooper

(57) ABSTRACT

Combining an implant and cement for prophylactic and/or preventative use for femoral neck augmention. A hole is drilled into the femoral neck. The hole is filled with an uncured filler cement after loose materials have been removed from the hole. Then, an open-ended tube, an implant, having openings through its walls is inserted into the hole and attached to the bone. Finally, additional filler cement is provided under pressure to the inside of the tubular implant. The filler cement flows into spaces in the bone structure via the tube wall openings. A sliding leak-tight fit between the implant and a cement injection tube permits delivery of cement at preselected locations along the implant length. Pressure is maintained until the filler cement has hardened. A strengthening factor up to 3 was measured when osteoporotic bone was strengthened.

40 Claims, 7 Drawing Sheets

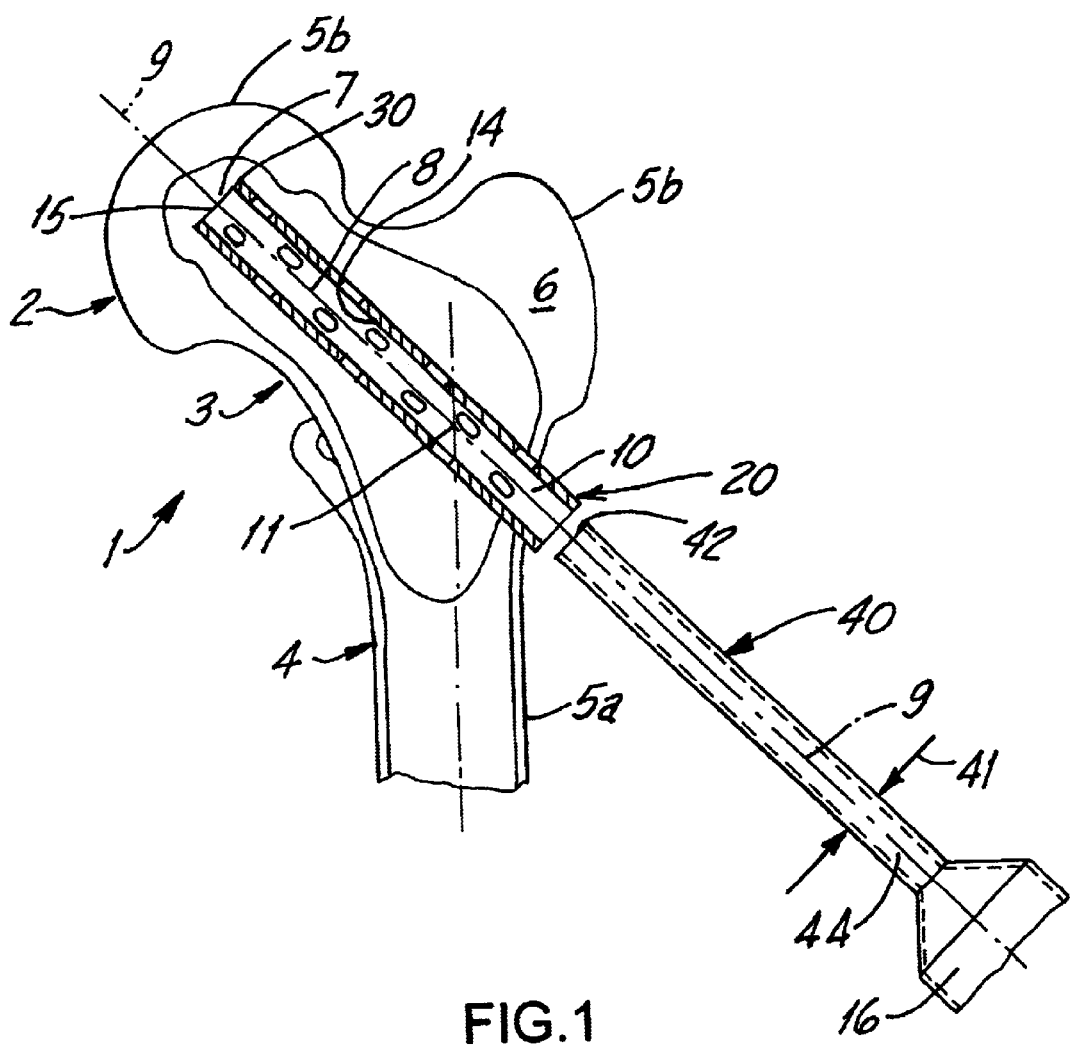
FIG.1
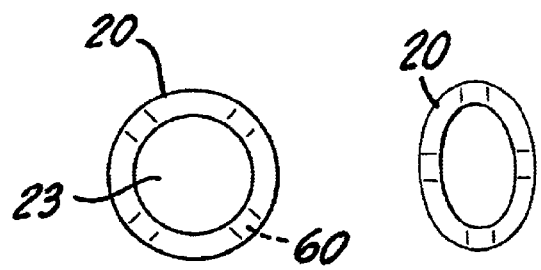 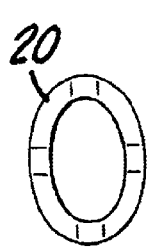 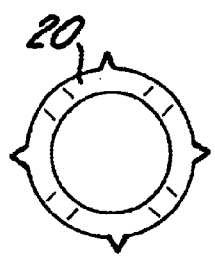
FIG.5a  FIG.5b  FIG.5c

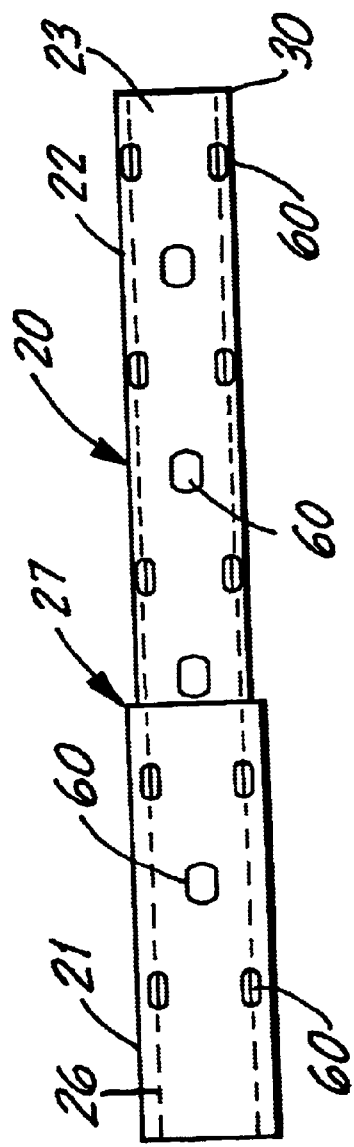
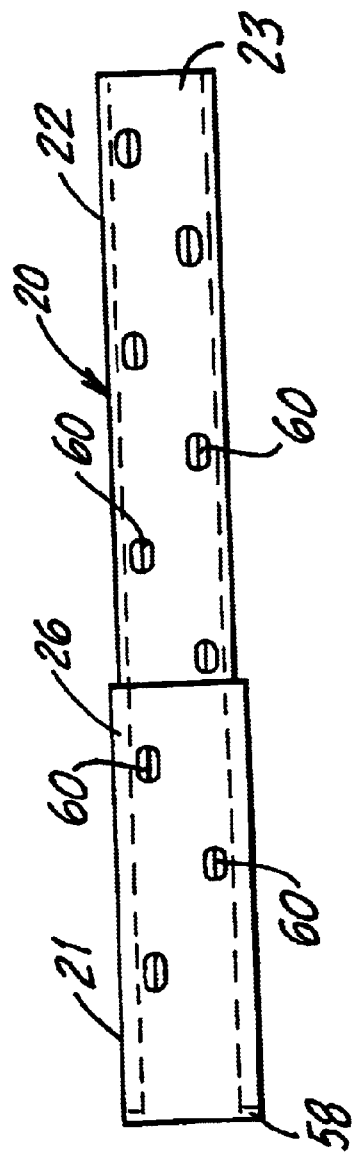
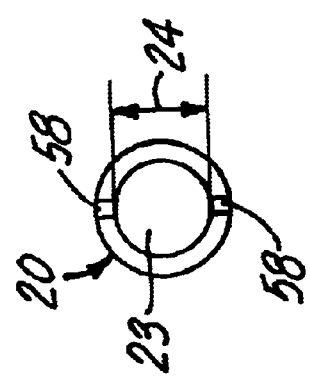
FIG.2a
FIG.2b
FIG.2c

METHOD AND APPARATUS FOR AUGMENTATION OF THE FEMORAL NECK

This application claims the benefit of provisional application No. 60/315,577 filed Aug. 28, 2001.

BACKGROUND OF THE INVENTION

Femoral neck fractures are a major source of morbidity and mortality in the elderly population. Ninety-eight percent of all hip fractures occur in people over the age of fifty, with the average age being seventy-nine for females and seventy-four for males. By age ninety, thirty-two percent of all females and seventeen percent of all males in the United States will have sustained a hip fracture. Hip fractures occur at a frequency of 9.6/1000 people—translating into 240,000 hip fractures per year in the U.S. alone. Due to the increase of the elderly population, the projected conservative estimates predict that by the year 2040, there will be 520,000 hip fractures per year. The risk of sustaining a second hip fracture is increased nine fold (from 1.6/1000 to 15/1000), and six fold in females (from 3.6/1000 to 22/1000).

Hip fractures are the number one cause of accidental death in the U.S. in the age group over 75. There is a twelve percent decrease in a person's life expectancy after sustaining a hip fracture with the greatest mortality occurring in the first four to six months. Between fourteen to thirty-six percent of all hip fracture patients die in the first year post injury. Only sixty-four percent of the patients return to the community and twenty percent will not regain the ability to ambulate without assistance.

Medical cost from hip fractures are a significant strain on our already over-taxed healthcare system.

The femoral neck poses a difficult problem to the elderly patient and the treating orthopedic surgeon. During the aging process, in general, endosteal and outer periosteal diameters increase as a protective mechanism. As the bone mass shifts further from the epicenter, skeletal strength is maximized despite a decrease in bone mass. However, similar protective mechanisms do not occur in areas of cancellous bone (i.e., the femoral neck). In addition, the femoral neck is deficient in periosteum and is, therefore, unable to compensate for loss of endosteal bone by periosteal bone formation. When an elderly patient falls, it is estimated that approximately 3700 kg-cm of energy must be dissipated. The femoral neck can only absorb approximately 60 kg-cm of energy prior to fracture. Most of the energy in a fall is absorbed by active muscle contractions. In an elderly patient, the neuromuscular response cannot act quickly enough to dissipate the kinetic energy. Consequently, when the level of stored energy in the neck exceeds its threshold, a fracture develops.

Treatment of femoral neck fractures is a challenge for orthopedists despite progress in practice and technology, particularly with osteoporotic bone. Femoral neck fractures are usually repaired using hip screws or an angled blade plate, both techniques requiring a metallic plate fixed to the lateral femur through cortical screws. Substantial surgery is associated with lateral places. The surgery usually stiffens the femur laterally but risks overloading the lateral femur. Either procedure may not provide enough stability at the fracture site in osteoporotic bone. These treatments are only used as post-fracture curatives. No standard procedure is performed to prevent femoral neck fractures, although Crockett in 1960 proposed pinning the femoral neck for prophylactic use.

A limited number of reports investigated prophylactic strengthening of an intact femoral neck. Beside medical measures, Crockett (1960) suggested pinning, using a pin of 4 mm, the femoral neck of high-risk patients. Pinning the femoral neck along the neck axis strengthens most effectively against shear stresses. Crockett supported his contention that pinning intact femora can effectively strengthen the femoral neck through experiments. In addition to the risk of shear fracture of the femoral neck, delamination between cortical (cortex of the bone) and cancellous bone remarkably reduces mechanical strength of the femoral neck composites (cortical and cancellous bone). The risk of delamination is highest at the interface of cancellous to cortical bone. Delamination risk can therefore be reduced if the interface and the supporting cancellous bone are strengthened.

Franz, et al. (February 2001) presented at the $47^{th}$ meeting of the Orthopaedic Research Society a study investigating the feasibility of injecting low-viscosity bone cement into the proximal femur and determining the corresponding augmentation effect. In their study, Franz, et al. drilled a 3.5 mm canal along the femoral neck axis. Bone cement was injected using a 4 mm biopsy needle. Although this study showed improved capacity of injected femora to withstand larger forces prior to fracture if compared to contra-lateral femora, there was a rise in temperature due to curing cement, and unpredictable long-term behavior of cements. These factors prevented current use of this technique as prophylactic measures for reducing fracture risk of the femoral neck. Although filling the proximal femur with bone cement can effectively reduce delamination fracture of the femoral neck, limited shear capacity of bone cement remains unpredictable for long-term use. Although the cement injection was monitored, there was no mechanism to control injection.

The above data clearly shows that a new effective and widely applicable strategy to prevent hip fracture is urgently needed. Medical treatment to prevent femoral neck fractures, as well as other fractures in the elderly have been geared with guarded effectivity to decreasing the rate of bone mass loss by either hormonal therapy (i.e., estrogen), by calcium supplementation, and by weight bearing exercises. Surgical treatment has been used solely as a post-fracture modality in the treatment of femoral neck fractures. To date, no surgical technique has been developed to prevent femoral neck fractures from developing.

References
1. Crockett, GS (1960). *Osteoporosis in the Elderly. Clinical Practice.*
2. Franz, T; Heini, PF; Frankhauser, C; Gasser, B (February, 2001). *Reinforcement of the Osteoporotic Proximal Femur Using PMMA Bone Cement—An In Vitro Study.* $47^{th}$ Orthopaedic Research Society. P. 0989, San Francisco, Calif.

SUMMARY OF THE INVENTION

An objective of this invention is to develop a method and apparatus of a femoral neck augmentation technique. The goal is to strengthen the femoral neck sufficiently to withstand a larger amount of force prior to fracture, utilizing a minimal invasion procedure. Traditional methods of surgical instrumentation are being used to fix the femoral neck fracture. Most of these methods require substantial surgical and anesthetic procedure. None of these methods can be used as a prophylactic method to augment the bone and prevent an impending fracture.

The proposed invention provides a new method of surgical prevention, by performing a minimal novel surgical procedure before a fracture occurs. Thereby, a bigger and more complicated procedure may be prevented.

The method includes percutaneous injection of uncured plastic material into the weakened femoral neck, before a fracture occurs. First, a hole is drilled into the femoral neck. The hole is filled with an uncured filler cement after loose materials have been removed from the hole. Then, an open-ended tube, an implant, having openings through its walls is inserted into the hole and attached to the bone. Finally, additional filler cement is provided under pressure to the inside of the tubular implant. The filler cement flows into spaces in the bone structure via the tube wall openings. Pressure is maintained until the filler cement has hardened.

Materials, which are currently used in surgery in the body, are used as the implant and cement for femoral neck augmentation. The filler cement has a degree of resilience and the capability of adhering to bone and the implant. The tubular implant and filler cement are less rigid than pins and screws, allowing the bone-cement construction to absorb energy prior to fracture.

The present invention relates to a cannulated implant that prophylactically strengthens an intact osteoporotic femoral neck which is at high risk of fracture. The cannulated implant is placed in the bone along the femoral neck axis and features outer surface openings, designed for extrusion therethrough of bone cement into femoral bone regions affected by osteoporosis. Bone cement penetrates into the femoral head, femoral neck and proximal femur. Implant and cement, penetrated into cancellous bone, strengthen the proximal femur and reduces risk of femoral neck fractures.

This invention is a hybrid technique (implant and cement) combining an implant and cement for prophylactic and/or preventative use, although the technique can be used as post-fracture curative and/or palliative procedure. Preventative effect of the new technique exists in that the implant, connected to cement penetrating adjacent cancellous bone, strengthens the femoral neck to withstand greater force prior to fracture. This technique requires no lateral plate, thus minimizing surgery and reducing lateral load shift. Cement extruded through the implant into cancellous bone intimately connects the implant with bone, stabilizing and strengthening the proximal femur prior to fracture. If fractures can be prevented there will be less hospital admissions and prorogated health care, benefiting both surgeons and patients.

The present invention introduces a new technique that strengthens against delamination as well as shear fractures. It combines (a) using a cannulated implant strengthening the femoral neck against shear fracture and (b) injection of plastic material, through the hollow implant with openings at the surface, into the femoral neck. The cement penetrates up to the neck cortex and strengthens against delamination fracture. This invention also features a method and apparatus that locally controls and directs cement extrusion into the surrounding bone.

Recent experimental results by the inventors support the convention of prophylactically strengthening the femoral neck prior to fracture. A strengthening factor up to 3 was measured when osteoporotic bone was strengthened. It is concluded from this study that this technique (implant and cement) is most effective when applied as a preventative measure to patients with a high degree of osteoporosis. This technique can also be used to stabilize femoral neck fractures.

Still further objects and advantages of the invention will be apparent from the specification.

The invention accordingly comprises the several steps and the relation of one or more of such steps with respect to each of the others, and the apparatus embodying features of construction, combinations of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a fragmentary semi-schematic view, partially in section, of the apparatus and represents an instant during the method in accordance with the invention for augmenting the femur with cement and an implant;

FIGS. 2a–c are three orthogonal views of an implant in accordance the invention;

FIGS. 5a–c illustrate variations for implant cross-sections;

Figure 3A:
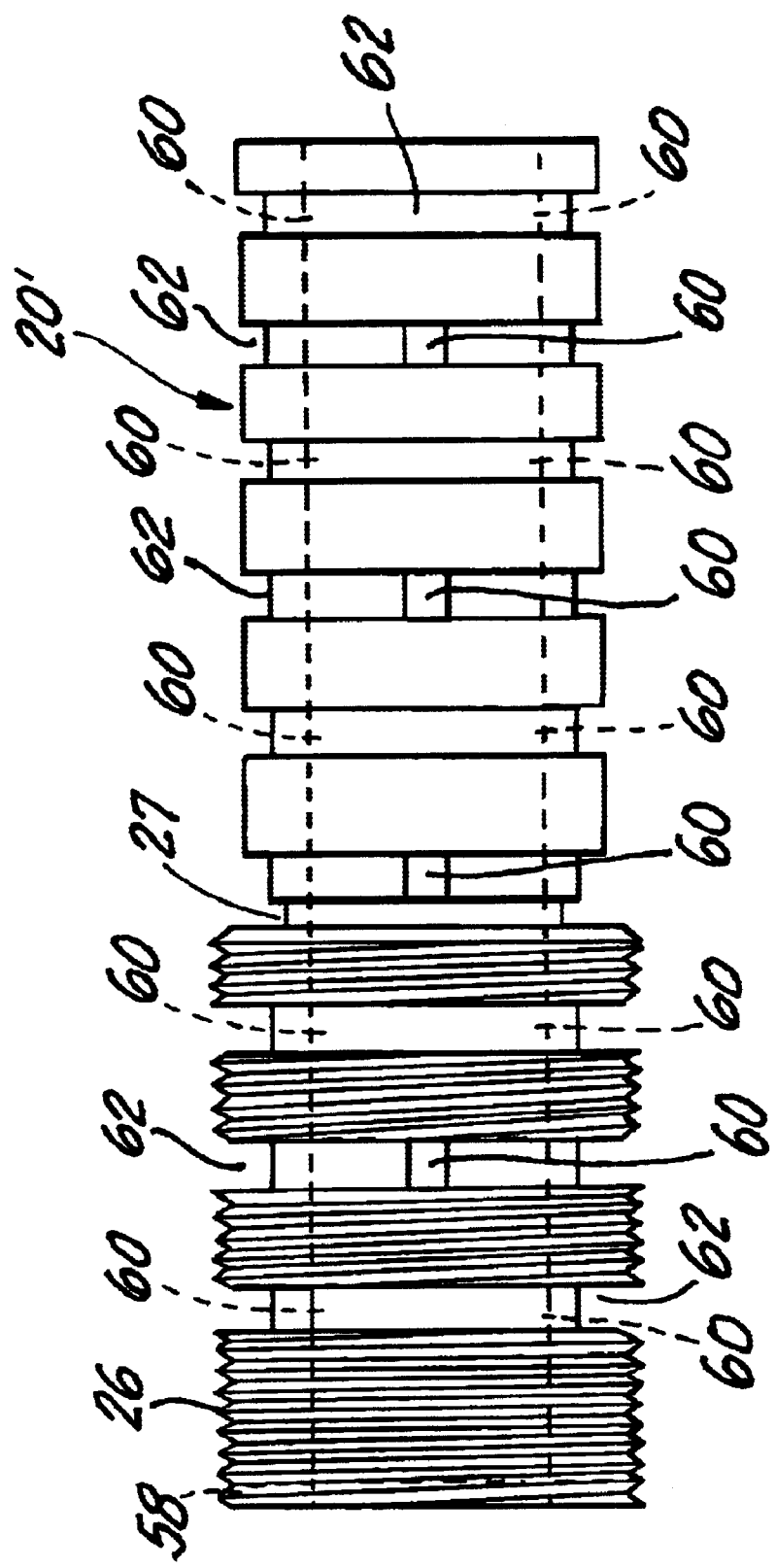
FIGS. 3a–b is an alternative embodiment of a circular implant in accordance with the invention in elevation and diametric section.

The figures are not drawn to scale.

DESCRIPTION OF PREFERRED EMBODIMENTS

With reference to FIG. 1, the femur 1 (thighbone) features a proximally rounded head 2. The proximal femur 1 has a long shaft 4. The femoral neck 3 connects to the femoral head 2 and shaft 4. The femur 1 features a hard thin shaft cortex (shell) 5a that is remarkably thicker than the cortex of the neck 5b. The proximal femoral cortex is filled with spongy-like bone (cancellous bone) 6. A line 9 connects the head center 7 to the center of the femoral neck 8 and is named the axis of the femoral neck. The projection of the line 9 to the lateral femur cortex is called the drilling starting point 10.

The invention includes a hollow implant 20 and injection tube 40. The implant 20 has two portions, a lateral portion 21 and a medial portion 22, also called the implant shaft. The implant has a longitudinal continuous hole 23 through its lateral and medial portions. The injection tube 40 has an identical geometrical cross-section shape as compared to the profile of the implant hole 23. The continuous hole 23 is circular; the injection tube 40 is also circular. The outer dimension 41 of the injection tube 40 is slightly smaller than the inner dimension 24 of the hole 23 to provide a tight but sliding fit as described more fully hereinafter. The injection tube 40 has thin wall thickness to maximize the tube inner dimensions. The larger the inner dimensions of the tube, the less pressure is required to extrude cement into cancellous bone. The lateral portion 21 of the implant 20 has a screw thread 26 along the length of the lateral portion to fix the lateral portion 21 into the femoral cortex 5a. The implant 20 may feature a mechanical weakening; e.g., a circumferential groove (not shown for clarity in FIG. 1 but located at 27) between the medial and lateral portions 21,22 of the implant 20. The weakening permits flexure and prevents transferring large bending moments to the lateral femur. The lateral portion 21 of the implant 20 includes a slot 58 that serves when connecting a screwdriver to insert and fix the lateral portion of the implant into the femoral cortex 5a. The implant 20 has openings 60 through the tube wall on its lateral portion 21 (see FIG. 2) and medial portion 22 connecting to said continuous hole 23 of the implant. The openings 60 on the implant 20 are distributed circumferentially and longitudinally over the implant surface. The openings 60 at the lateral portion 21 of the implant 20 extend through the screw thread portion 26.

Figure 3B:
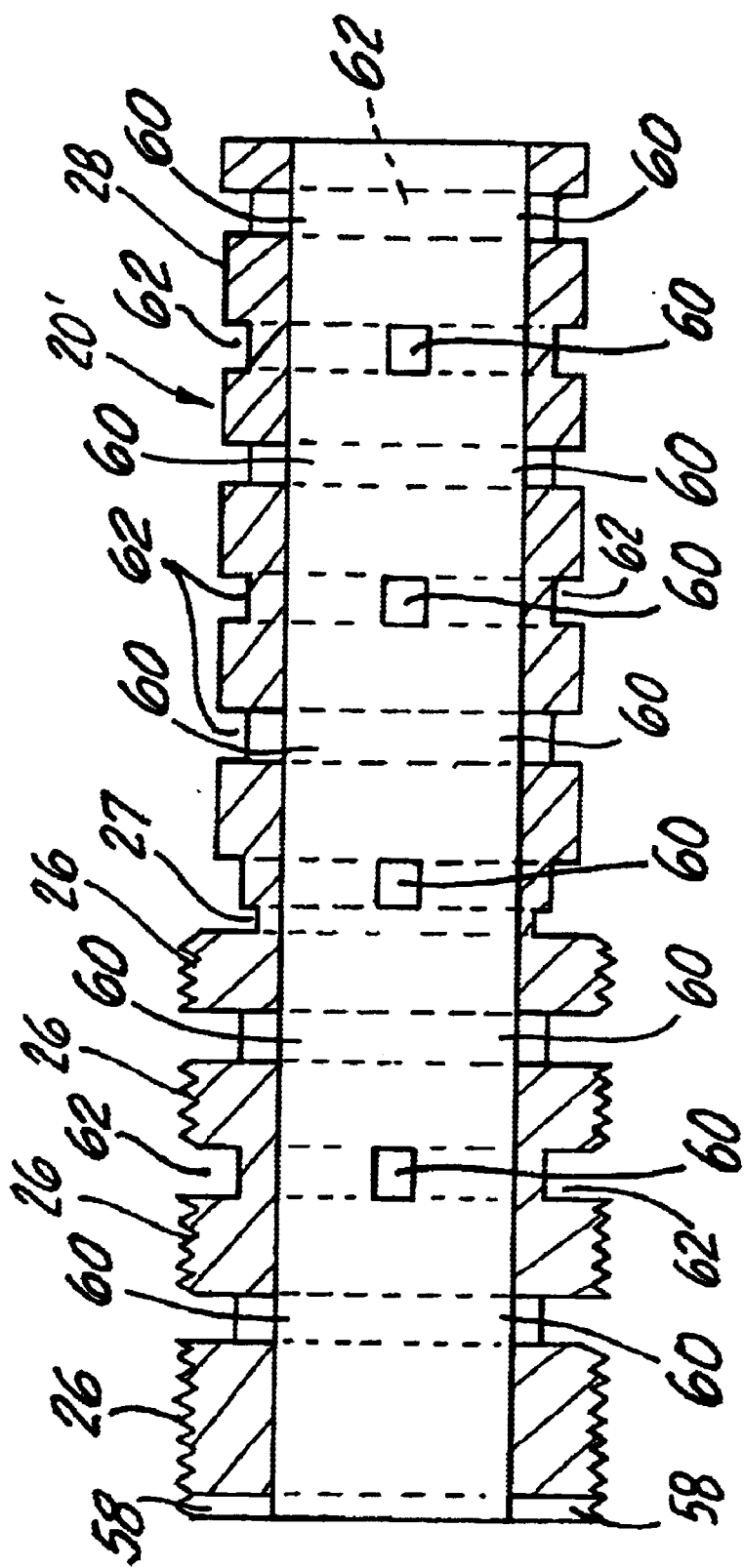

In an alternative embodiment (FIGS. 3a–b) in accordance with the invention, the rectangular holes 60 in the lateral and medial portions of the implant 20' are recessed in circular grooves 62 in the outer surface 28 of the implant shaft. The grooves 62 extend circumferentially between openings 60 and traverse adjacent openings 60. The grooves may also extend longitudinally and diagonally between openings. A weakening groove 27 is located between the medial and lateral portions. The quantity of holes 60 at each longitudinal groove location is not limited to two (illustrated).

In an augmentation method of this invention:
(1) A continuous hole 14 (FIG. 1) of the same outer dimensions as the implant 20 is created along the femoral neck axis (9). The hole 14, at its proximal/medial end 15, does not reach the thin femoral head cortex (5b).
(2) The hole 14 is then flush-washed with saline solution to clean the hole of bone abrasions and fat tissue. In addition to flush washing, a sucking (vacuum) technique is used to further clean the hole 14.
(3) Cement is prepared (3 to 4 commercial portions) and poured into a syringe (not shown) connected to the injection tube 40 through an adapter 16. The hole 14 created along the femoral neck axis 9 in step (1) is next completely filled with cement.
(4) The implant 20 is then carefully placed into the hole 14 and cement. The medial portion 22 of the implant 20 slides into the hole 14, while the lateral implant portion 21 is threaded into the bone.
(5) The injection tube 40 is next completely inserted in the hole 14 by sliding into the implant 20 until the injection tube tip 42 reaches to the medial end 15 of the hole 14, 23. Cement in the syringe and injection tube 40 is then pressurized by applying pressure on the syringe plunger. Cement is thereby pressed through the tube 40 and passes axially through the implant end 30 into the surrounding bone of the femoral head 2, the cement flowing and distributing directionally from the injection tube tip 42 and implant 20 in accordance with the local levels of bone porosity.

The pressurized injection tube 40 is then pulled back gradually until its tip 42 approximately reaches the region of the femoral neck center 8. There a large portion of cement is forced through the tube 40, passes radially through the implant openings 60 on the implant 20 and penetrates into surrounding cancellous bone 6 of the femoral neck 3, whereby the neck 3 is completely filled with cement.

To complete the filling procedure, the tube tip 42 is pulled back until it reaches the region 11 of the femoral axis 9. Any cement left in the syringe is then completely extruded around the implant 20 into the surrounding cancellous bone.
(6) The cement is brought to its hardened state by means suited to the particular cement that is utilized.
(7) The distal end (exposed) of the implant 20 is trimmed of excess material, as may be required, and the original incision that provides access for forming the hole 14 of step (1) is closed for healing.

The openings 60 of the implant 20 and grooves 62 in conjunction with the injection tube 40 facilitate local pressurization and cement distribution at the bone/implant interface. The injection tube 40 is selectively positioned at the locations of the implant 20 where it is desired that the cement should be pressurized. The injection tube 40 has a large diameter (thin wall) continuous hole 44 so that controlled cement extrusion is achieved. The space between the outer dimensions of the injection tube 40 and the internal dimensions 24 of the implant 20 is large enough so that air escapes during cement injection, but small enough that the cement does not go back through this generally annular space.

When cement is extruded through the tube 40 and close to the openings 60, cement penetrates into adjacent grooves 62. Thereby the grooves 62 connected to openings 60 produce a local cylindrical area of cement around the implant shaft of homogeneous pressure. The area of homogenized pressure improves the area and depth of penetration of cement into the bone. In addition, the local pressurization facilitates controlled distribution of cement into the surrounding bone. The grooves 62 and openings 60 further strengthen the physical connection between the cement, implant, and infiltrated cancellous bone. The implant may feature a groove (not shown) close to its tip 30. This groove is circular and cuts through adjacent openings 60. The implant tip 30 may feature an extended thread (not shown) in addition to the groove.

The following remarks may in part be repetitious of the above, nevertheless they describe important features. FIG. 3 is similar to FIG. 2 but clearly indicates that irregularities may be formed on the outer surface of the implant, whether elevated above or penetrating the surface. These irregularities provide better adhesion for the cement with the implant and provide further holding engagement with the bony structure. As stated, cement distribution and penetration are enhanced.

The implant may be made of metal, for example, stainless steel, titanium, tantalum, nickel-cadmium and other metal alloys. The implant may be made of plastic and may even be made of the same material as the cement that is used for bone augmentation. On the other hand, an implant plastic may differ from the cement, and may be a composite material that is reinforced, for example, with rods, fibers, wires, whiskers, etc. as known in the plastic arts. The implant may be laminated of different materials. Ceramic materials that are altered in composition so as to have a degree of resiliency may also be used.

In both physical construction and in the material selection, the practitioner and manufacturer must be aware of the required non-toxic properties of the material. There must be no long time local toxicity. An opportunity for bony ingrowths into the insert is very desirable.

The cement material must have a suitable liquidity before curing so that it is readily injectable through the inlet opening into the hollow center of the implant. The plastic, elastic and mechanical qualities of the cement after curing must be considered. There must be minimal degradation with time of the performance characteristics of the implant and the cured cement. An ability to augment both the cement and the implant with fibers, whiskers, and the like, must be considered. The implant and the cement may each be combined with a material having a positive bone growth factor included. Detectability of the materials when exposed to x-ray or used in a CT scan or magnetic resonance imaging device, must also be considered.

Nevertheless, it must be noted that in spite of the many parameters which can differ based upon the patient and/or the preferences of the manufacturer and practitioner, the basic method steps and constructions in accordance with the invention remain applicable.

The sliding connection between the cement filled injector tube and the implant that is positioned within the bone must be leak tight to a degree that the cement can be pressurized and air can escape (with no or little leakage of cement at the connection) as cement is urged into the center of the implant. The cement passes through the axial and lateral flow openings of the implant to fill and engage cavities in the bone, and to fill the implant itself.

Many types of connection between the bone and the implant will be suitable. The connection is not limited to a particular type although in development testing of the present invention a threaded connection was found to provide favorable results in preventing leakage of cement and loss of pressure on the cement while filling and hardening the cement.

Although many materials may be used as cement, presently preferred is polymethylmethacrylate (PMMA), which was used with good results in development testing of the present invention. This material provides approximately 12 minutes of working time from a liquid state to a hardened cement after the elements to produce the cement have been mixed together. Pressure was maintained on the cement during the curing process in the bone cavity and insert.

It is understood that some materials that may serve as cement may expand on curing and other materials may be dimensionally stable or may contract. An expanding cement is preferred, as it will assist in penetrating the bony structure with cement.

When cement is first inserted into the drilled opening (hole) formed in the bone, before the implant is put in place, the cement is initially delivered at the proximal end (deepest into the bone) of the hole so that air may readily escape from the opening as well as bone chips, fatty materials, etc., that may remain. The cement injection tube is gradually withdrawn as the hole fills.

Making the implant of pre-stressed materials may be advantageous where the material is otherwise brittle in tension. Thus, similar to pre-stressed concrete, pre-tensioned reinforcement within the brittle material may permit use and give the material resilient load bearing qualities.

During practice of the method, the implant may be inserted with the distal end substantially externally flush with the bony structure so that the implant is in its final position, or the implant may be slightly extended from the bone surface to allow for convenient interface with the cement source. After the cement has set, the practitioner can physically modify any extending portions of the insert to suit his preference and the needs of the particular situation.

Figure 4A:
FIGS. 4a–d illustrate surface variations for medial portions of implants.
Figure 4B:
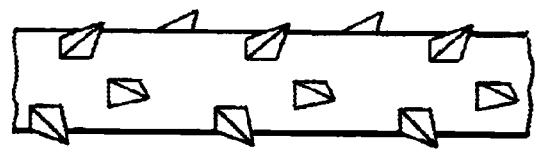

Round holes 60 are illustrated in implants in several figures (land 4*a*). An implant may have holes of any shape through its walls. Tabs or spurs of different shapes that are, for example, punched through the surface may also be used (FIG. 4*b*). Such features provide openings for flow of cement from the center of the implant to the bony structure, and also provide a good grip that resists removal of the implant once it has been inserted into the bony hole or socket that has been prepared for it.

Figure 4C:
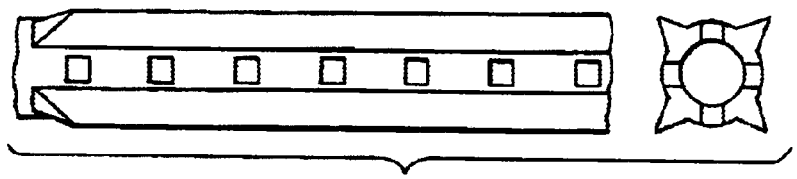

FIG. 4*c* illustrates that the implant need not be round in cross section. The best shapes will in time be determined from continued use of this method. However, it is expected that the patient's bone structure and the practitioner's preferences will in large measure determine the contours of the implant that is selected and inserted in the femur.

FIGS. 5*a–c* show end views of implants to illustrate that they may be round or oval, and almost any imaginable shape that will fit within the contours of the bone. However, regardless of the shape of the implant's cross-section, the cross-section of the injection tube must be substantially congruent and provide the sliding fit that permits air to escape with a minimum of cement leakage or pressure loss. Such a fit may be provided based on filling procedures using a particular cement. Suitable clearance may be provided along the entire perimeter of the implant/insertion tube interface. On the other hand, a tight sliding fit may be locally relieved (not illustrated) for escape of air by longitudinal grooves, slots, flutes, etc. of small cross-section on one or both surfaces, while still minimizing escape of cement because of the greater viscosity of the cement (compared to air).

Figure 4D:
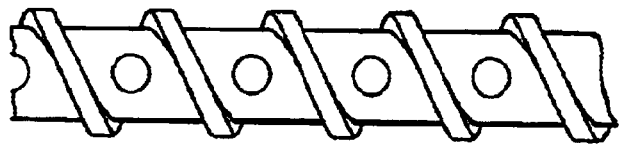

FIG. 4*d* indicates an implant that threads itself into a hole provided in the bone so that the implant is not easily removed from the bone. This implant, like every other implant in accordance with the invention, will also have lateral openings through its surface.

The surfaces of all implants may be roughened, textured, porous, etc. for better engagement and integration in time with the bony tissues. Bone growth factors may be included in the surface or throughout the implant material (and in the cement).

Figure 6A:
FIGS. 6a–c illustrate reinforcement elements for augmenting the femur in combination with a cement.
Figure 6B:
Figure 6C:
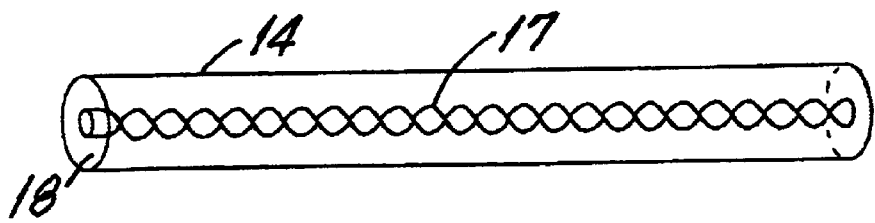

FIGS. 6*a–c* illustrate reinforcement means 17 inside the central hole 14 formed in the femur, which otherwise is filled with cement 18 that also penetrates the surrounding cancellous bone. After the cement has been injected in the hole 14 and cures, the reinforcement means becomes a permanent reinforcement for the cement.

The cement is selected for its viscosity, handling and setting time, and strength after curing (polymerization or precipitation, etc.). The cement changes from a liquid to a solid phase in an operating time frame based on various physical effects, e.g. temperature, heat. The cement 18 may be a bone or dental cement, polymer, elastomer, and absorbable and biodegradable materials, and may combine bone growth factors and other elements enhancing biocompatibility. The cement provides adhesion to bone tissue and to the reinforcement 17. The cement may include particles, fibers, etc., improving the shear properties.

The reinforcement 17 is an elongated body, e.g., circular or elliptical rod, of any geometrical form featuring outer dimensions similar to the hole 14. By inserting the elongated body 17, the cement in the hole 14 is pressurized to fill radial spaces between the body 17 and surrounding bone. Pressurized cement also penetrates into adjacent cancellous bone when the elongated body 17 is inserted.

The reinforcement 17 is made from solid material(s), e.g., cement, metals, composites, fiberglass, cement reinforced with wires, composites of synthetic polymers, porous biodegradable materials, or moldable, hand-shapeable material suitable for strengthening the femoral neck.

The reinforcement 17 may be prefabricated from the same cement material as is used subsequently in flowable state to fill the hole 14. The reinforcement intimately connects with surrounding cement by, e.g., grooves, keys, threads, roughened surface. A laminated elongated body made of layers may be used. Outer surfaces of the laminated, elongated body may have adhesive characteristics similar to the filling cement, whereby they connect to each other. A twisted wire is used in FIG. 6*c*.

Figure 7:
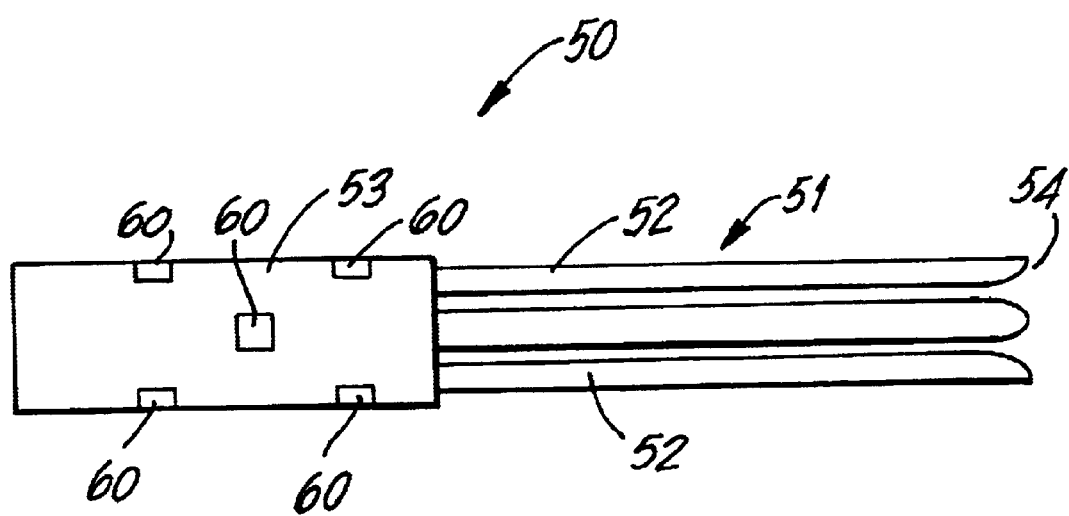
FIG. 7 is an alternative implant in accordance with the invention.

FIG. 7 illustrates another implant 50 in accordance with the invention where in the medial portion 51 fingers 52 extend from the mid-portion of the implant toward the proximal end 54 and provide a more flexible arrangement than those implants already illustrated. Each finger 52 extending toward the proximal end 54 is in effect a cantilever beam with a free end and each finger has good strength with flexibility. Additionally, the ability of the cement to readily flow into the bony structure is enhanced by this construction. The outer dimensions of the injector tube 40 also correspond with the inner dimensions of the lateral portion 53 and of the fingers 52 to provide a continuous tight sliding fit as required for filling the implant with cement. The lateral portion 53 includes through holes 60 and may also include surface grooves 62.

Figure 8:
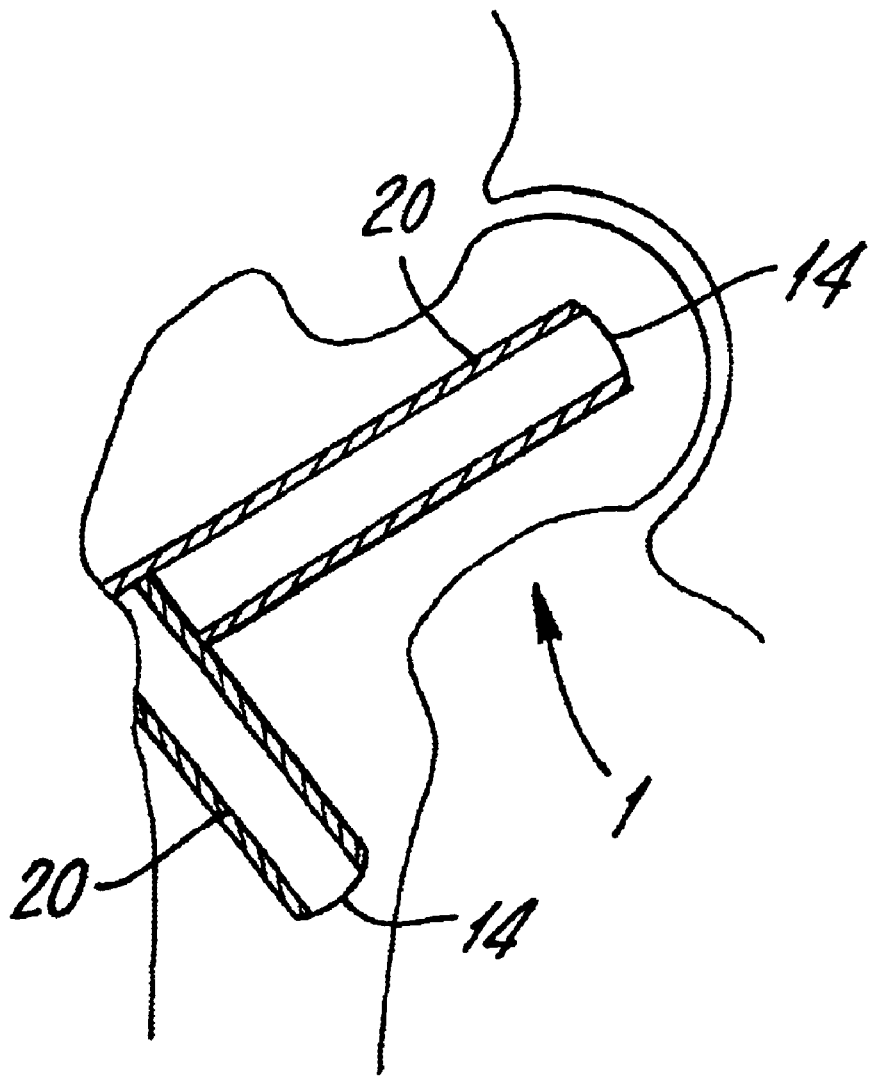
FIG. 8 illustrates a femur augmented at two locations in accordance with the invention.

FIG. 8 illustrates that more than one implant 20 may be inserted in respective holes 14 formed in the same joint 1 using the methods and apparatus of the present invention.

In development of the present invention, one of many favorable results was achieved using a circular cross-section biocompatible stainless steel implant having a length of 110 mm, an outside diameter of 12 mm where unthreaded and 14 mm where threaded. Thread pitch: 16 per inch. The medial portion (22) length: 70 mm; lateral portion (21) length: 40 mm. Inside diameter: 8 mm. Openings 60 were generally rectangular 3 mm×5 mm spaced longitudinally in nine circumferential bands.

The cement injection tube 40 was copper with clearance for sliding along the internal implant surface in the approximate range of 100 to 200 micrometers, assuming concentricity. Air was able to escape but not the cement. 40 to 50 ml of cement was injected in the experiments.

It is presumed that implants would, in time, be provided by a manufacturer in a kit also including a properly mating injection tube that assures a pressurizing sliding seal. Various lengths, diameters, cross-sections, materials, etc., would be available in a kit of elements.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method for installing an implant in a bony structure of a subject's body, said structure requiring one of reinforcement and repair, comprising the steps of:
    a) forming a hole in said bony structure and removing debris-product of said forming from said hole;
    b) inserting an implant having a generally cylindrical wall into said hole, said implant being a hollow tube having a distal end, proximal end and having a length substantially coextensive with a depth of said hole, said implant having an external cross-section substantially similar to a cross-section of said hole, said implant further having a plurality of openings through said implant wall distributed along said wall length;
    c) filling said hollow implant tube with flowable cement under pressure, said tube wall openings permitting lateral flow of said cement from said hollow tube into said bony structure, said cement flowing from an injection tube having a discharge end inserted inside said implant with an internal interface between said hollow tube wall and said injection tube that is substantially tight against cement leakage from a distal end of said implant to maintain said pressure, said discharge end being movable along said implant length;
    d) bringing said cement in said implant and said cement in said bony structure to a non-flowable state.

2. A method as in claim 1, further comprising the step between steps a) and b):
    2a) adding cement in a flowable state to at least partially fill said hole.

3. A method as in claim 2, wherein said hollow tube implant has an axial opening at said proximal end.

4. A method as in claim 2, wherein said openings through said implant wall are distributed peripherally around said tube.

5. A method as in claim 2, wherein in step d) said cement is maintained under pressure during transition from said flowable to said non-flowable state.

6. A method as in claim 2, wherein prior to step c) a first pressure seal is provided between said implant and said bony structure at said distal end of said implant at an entrance to said hole.

7. A method as in claim 6, wherein said first pressure seal is a threaded connection between said bony structure and said implant at said hole entrance.

8. A method as in claim 6, wherein said injection tube through which said flowable cement is discharged from said delivery unit, has a cross-section similar to an internal cross-section of said hollow implant, a close sliding fit existing between said implant and said injection tube, said close sliding fit providing said second pressure seal against cement leakage.

9. A method as in claim 8, wherein said close sliding fit permits escape of air from the hollow implant.

10. A method as in claim 2, further comprising the step of providing a cement delivery unit including said injection tube, said injection tube having a cement discharge opening for dispensing cement in said flowable state in step c), said cement being deliverable by locating said discharge opening at selected positions along said implant length, said internal interface providing a second pressure seal between said implant and said cement delivery unit reducing potential escape of delivered cement and maintaining pressure on said cement during cement delivery in at least one of step c) and step d).

11. A method as in claim 10, wherein said delivery unit commences delivery in said steps 2a) and c) at a proximal end of said hole and continues delivery progressively closer to said distal end of said hole, said delivery location moving at least one of continuously and incrementally until said implant is filled to a pre-selected level.

12. A method as in claim 11, wherein said injection tube has at least three stationary rest locations while adding cement in step c).

13. A method as in claim 2, wherein said implant is constructed of the same material as said cement.

14. A method as in claim 2, wherein said openings may be of various shapes including round, oval, rectangular, triangular, generally polygonal, curvilinear, and combinations thereof.

15. A method as in claim 2, wherein at least a pair of said openings is connected together by a groove formed in an external surface of said implant wall.

16. A method as in claim 2, wherein said implant includes a plurality of cantilevered fingers extending longitudinally from a cylindrical portion of said implant towards said proximal end, said openings including spaces between said fingers.

17. A method as in claim 1, where said hollow tube implant has an axial opening at said proximal end.

18. A method as in claim 1, wherein prior to step c) a first pressure seal is provided between said implant and said bony structure at said distal end of said implant at an entrance to said hole.

19. A method as in claim 18, wherein said first pressure seal is a threaded connection between said bony structure and said implant at said hole entrance.

20. A method as in claim 18, wherein said injection tube through which said flowable cement is discharged from said delivery unit, has a cross-section similar to an internal cross-section of said hollow implant, a close sliding fit existing between said implant and said injection tube, said close sliding fit providing said second pressure seal against cement leakage.

21. A method as in claim 20, wherein said close sliding fit permits escape of air from the hollow implant.

22. A method as in claim 1, further comprising the step of providing a cement delivery unit including said injection tube, said injection tube having a cement discharge opening for dispensing cement in said flowable state in step c), said cement being deliverable by locating said discharge opening at selected positions along said implant length, said internal interface providing a second pressure seal between said implant and said cement delivery unit reducing potential escape of delivered cement and maintaining pressure on said cement during cement delivery in at least one of step c) and step d).

23. A method as in claim 22, wherein said delivery unit commences delivery in said step c) at a proximal end of said hole and continues delivery progressively closer to said distal end of said hole, said delivery location moving at least one of continuously and incrementally until said implant is filled to a pre-selected level.

24. A method as in claim 23, wherein said injection tube has at least three stationary rest locations while adding cement in step c).

25. A method as in claim 1, wherein in step d) said cement is maintained under pressure during transition from said flowable to said non-flowable state.

26. A method as in claim 1, wherein said implant is constructed of the same material as said cement.

27. A method as in claim 1, wherein said openings may be of various shapes including round, oval, rectangular, triangular, generally polygonal, curvilinear, and combinations thereof.

28. A method as in claim 1, wherein at least a pair of said openings is connected together by a groove formed in an external surface of said implant wall.

29. A method as in claim 1, wherein said implant includes a plurality of cantilevered fingers extending longitudinally from a cylindrical portion of said implant towards said proximal end, said openings including spaces between said fingers.

30. An implant for augmenting a bony structure comprising:
   a generally cylindrical hollow tube having length, said tube being for insertion in a hole formed in said bony structure, said tube having a distal end and a proximal end and being at least partially open axially at each said end;
   means for attaching said distal end of said implant to said bony structure at an entrance to said hole, in use of said implant a first pressure seal being formed between said implant and said bony structure;
   a plurality of openings through a cylindrical wall of said hollow tube for cement flow therethrough, said openings being distributed along said tube length substantially from said proximal end to said distal end;
   means within said hollow tube for connecting to a cement injection unit in a sliding engagement, said engagement being substantially leak-tight to said cement and permitting air to flow therethrough, said sliding engagement allowing delivery of cement from said injection unit through said implant openings directly at selected locations along said implant length.

31. An implant as in claim 30, wherein a cross-section of said hollow tube has external contours similar to a cross-section of said hole.

32. An implant as in claim 30, wherein said means for attaching to said bony structure includes external threads on a first portion of said implant proximate said distal end.

33. An implant as in claim 32, wherein a portion of said plurality of openings are located through said threaded portion of said implant.

34. An implant as in claim 30, wherein said openings may be of various shapes including round, oval, rectangular, triangular, generally polygonal, curvilinear, and combinations thereof.

35. An implant as in claim 30, wherein at least a pair of said openings is connected together by a groove formed in an external surface of said implant wall.

36. An implant as in claim 30, wherein said cement injection unit includes an injection tube through which said flowable cement is discharged from said delivery unit, and said means for connecting includes an internal cross-section of said hollow implant that provides said sliding engagement between said implant and said injection tube, said sliding engagement providing a second pressure seal against cement leakage.

37. An implant as in claim 36, wherein said sliding engagement permits escape of air from the hollow implant.

38. An implant as in claim 30, wherein said implant includes a plurality of cantilevered fingers extending longitudinally from a cylindrical portion of said implant towards said proximal end, said openings including spaces between said fingers.

39. A combination of an implant and a cement injection tube for augmenting a bony structure, said implant being a generally cylindrical hollow tube having an internal cross-section, said injection tube being an element for use in a flowable cement delivery unit and having an external cross-section similar to said internal implant cross-section, said injection tube being slidable to selectable positions within said implant for direct delivery of cement at said positions, an implant/tube interface providing a fit permitting flow of air through said interface and substantially preventing flow of cement through said interface at said selectable positions.

40. An implant for augmenting a bony structure comprising:
   a generally cylindrical hollow tube having length, said tube being for insertion in a hole formed in said bony structure, said tube having a distal end and a proximal end and being at least partially open axially at each said end;
   means for attaching said distal end of said implant to said bony structure at an entrance to said hole, in use of said implant a first pressure seal being formed between said implant and said bony structure;
   a plurality of openings through a cylindrical wall of said hollow tube, said openings being distributed along said tube length; and
   a plurality of cantilevered fingers extending longitudinally from a cylindrical portion of said implant toward said proximal end, said openings including spaces between said fingers.

* * * * *